United States Patent [19]
Holmgren et al.

[11] Patent Number: 6,019,973
[45] Date of Patent: Feb. 1, 2000

[54] HYBRID MOLECULES BETWEEN HEAT-LABILE ENTEROTOXIN AND CHOLERA TOXIN B SUBUNITS

[76] Inventors: Jan Holmgren, Korvettgatan 1 D, VästräFrölunda, Sweden, S-421 74; Michael R. Lebens, S-413 22 Drive Belfrages Väg 20, Göborg, Sweden, S-413 22

[21] Appl. No.: 08/952,337

[22] PCT Filed: May 2, 1996

[86] PCT No.: PCT/SE96/00570

§ 371 Date: Jan. 5, 1998

§ 102(e) Date: Jan. 5, 1998

[87] PCT Pub. No.: WO96/34893

PCT Pub. Date: Nov. 7, 1996

[30] Foreign Application Priority Data

May 5, 1995 [SE] Sweden .................................. 9501682

[51] Int. Cl.[7] .......................... A61K 39/00; A61K 39/02; A61K 39/108; A61K 39/106
[52] U.S. Cl. ..................... 424/185.1; 424/236.1; 424/241.1; 424/261.1; 424/184.1; 530/350
[58] Field of Search .............................. 424/183.1, 185.1, 424/236.1, 241.1, 261.1, 186.1; 530/350, 825; 514/867, 837

[56] References Cited

U.S. PATENT DOCUMENTS 4,758,655  7/1988  Houghten ................. 530/324

OTHER PUBLICATIONS

Backstrom et al. Mol. Microbiol. 24 (3): 489–497, 1997.

Lebens et al. Infect. Immun. 64 (6): 2144–2150, 1996.

J Clements. Infect. Immun. 58: 1159–1166, 1990.

*Primary Examiner*—James C. Housel
*Assistant Examiner*—S. Devi
*Attorney, Agent, or Firm*—Darby & Darby

[57] ABSTRACT

Hybrid molecules between heat-labile enterotoxin B subunit (LTB) and cholera toxin B subunit (CTB) are disclosed. Such a hybrid molecule comprises an amino-acid sequence which is composed of the amino-acid sequence of mature CTB in which such amino-acid residues are substituted with the corresponding amino-acid residues of mature LTB which impart LTB-specific epitope characteristics to said immunogenic mature CTB, or vice versa. In addition, a structural gene coding for such a hybrid molecule, a plasmid containing such a structural gene, and an immunogenic protein comprising such a hybrid molecule and optionally an immunoreactive amino-acid sequence of a prokaryotic or eukaryotic cell or a virus, are disclosed. Disclosed is also a vaccine, e.g. against enterotoxin-induced illness, comprising such an immunogenic protein, and a method of preventing or treating enterotoxin-induced illness in an individual.

13 Claims, 5 Drawing Sheets

```
         Asn     Val         Tyr     Leu         Ala
LTB: ATG AAT AAA GTA AAA TTT TAT GTT TTA TTT ACG GCG TTA CTA
CTB: ATG ATT AAA TTA AAA TTT GGT GTT TTT TTT ACA GTT TTA CTA
     Met Ile Lys Leu Lys Phe Gly Val Phe Phe Thr Val Leu Leu

Leu Cys             Ala         Ser         Glu
LTB: TCC TCT CTA TGT GCA CAC GGA GCT CCT CAG TCT ATT ACA GAA
CTB: TCT TCA GCA TAT GCA CAT GGA ACA CCT CAA AAT ATT ACT GAT
     Ser Ser Ala Tyr Ala His Gly Thr pro Gln Asn Ile Thr Asp
                                 +1

Ser                             Tyr     Ile
LTB: CTA TGT TCG GAA TAT CAC AAC ACA CAA ATA TAT ACG ATA AAT
CTB: TTG TGT GCA GAA TAC CAC AAC ACA CAA ATA CAT ACG CTA AAT
     Leu Cys Ala Glu Tyr His Asn Thr Gln Ile His Thr Leu Asn
             +10                                     +20

Leu                     Met
LTB: GAC AAG ATA CTA TCA TAT ACG GAA TCG ATG GCA GGC AAA AGA
CTB: GAT AAG ATA TTT TCG TAT ACA GAA TCT CTA GCT GGA AAA AGA
     Asp Lys Ile Phe Ser Tyr Thr Glu Ser Leu Ala Gly Lys Arg
                                     +30

Val                     Ser
LTB: GAA ATG GTT ATC ATT ACA TTT AAG AGC GGC GCA ACA TTT CAG
CTB: GAG ATG GCT ATC ATT ACT TTT AAG AAT GGT GCA ACT TTT CAA
     Glu Met Ala Ile Ile Thr Phe Lys Asn Gly Ala Thr Phe Gln
                     +40

LTB: GTC GAA GTC CCG GGC AGT CAA CAT ATA GAC TCC CAA AAA AAA
CTB: GTA GAA GTA CCA GGT AGT CAA CAT ATA GAT TCA CAA AAA AAA
     Val Glu Val Pro Gly Ser Gln His Ile Asp Ser Gln Lys Lys
     +50                                     +60

Thr
LTB: GCC ATT GAA AGG ATG AAG GAC ACA TTA AGA ATC ACA TAT CTG
CTB: GCG ATT GAA AGG ATG AAG GAT ACC CTG AGG ATT GCA TAT CTT
     Ala Ile Glu Arg Met Lys Asp Thr Leu Arg Ile Ala Tyr Leu
                             +70

Thr     Ile Asp
LTB: ACC GAG ACC AAA ATT GAT AAA TTA TGT GTA TGG AAT AAT AAA
CTB: ACT GAA GCT AAA GTC GAA AAG TTA TGT GTA TGG AAT AAT AAA
     Thr Glu Ala Lys Val Glu Lys Leu Cys Val Trp Asn Asn Lys
             +80                                     +90

Asn Ser                         Glu
LTB: ACC CCC AAT TCA ATT GCG GCA ATC AGT ATG GAA AAC TAG
CTB: ACG CCT CAT GCG ATT GCC GCA ATT AGT ATG GCA AAT TAA
     Thr Pro His Ala Ile Ala Ala Ile Ser Met Ala Asn ***
                                    +100
```

HYBRID MOLECULES BETWEEN HEAT-LABILE ENTEROTOXIN AND CHOLERA TOXIN B SUBUNITS

This application is filed as a § 371 application of PCT/SE96/00570, filed May 2, 1996 with a priority claim to national application 9501682-0, filed May 5, 1995 in Sweden.

The present invention relates to hybrid molecules between heat-labile enterotoxin B subunit (LTB) and cholera toxin B subunit (CTB). Immunogenic proteins comprising such hybrid molecules, optionally fused to immunoreactive amino-acid sequences of or from cells or viruses, may be used as immunogenic components in vaccines, e.g. in a broad spectrum vaccine against enterotoxin-induced diarrhoea.

BACKGROUND

Cholera remains an important cause of illness in many developing countries and has been estimated to result in more than 200,000 deaths each year. Infection with enterotoxigenic *E. coli* (ETEC) is the most frequent cause of diarrhoea in the developing world and amongst travellers; it is responsible for more than one billion diarrhoeal episodes and one million deaths annually. Infection with ETEC is also an important cause of disease in animals For both cholera and ETEC infections there is a great need for effective vaccines.

In both cholera and ETEC infections, the primary cause of diarrhoea is the action of an enterotoxin released by the infecting organisms in the intestine; in the case of cholera cholera toxin (CT) and in the case of ETEC heat-labile enterotoxin (LT). The two toxins are closely related both structurally and functionally, each consisting of a toxic A subunit (CTA or LTA respectively) surrounded by five identical B subunits (CTB or LTB respectively) (Spangler, 1992). The B subunit pentamers are responsible for the binding of the toxin to GM1 ganglioside receptors present on the surface of intestinal epithelial cells (Holmgren, 1981); LT can also bind to structurally related galactoprotein receptors (Holmgren and Fredman, et al., 1982).

Although both proteins may exhibit internal variation in a few amino-acid residues, e.g. in human versus animal ETEC isolates and in classical versus El Tor biotype cholera strains, LTB and CTB show a high degree of homology with 85% conservation of amino acids in the mature protein (FIG. 1) and there is evidence from crystallographic studies that LTB and CTB pentamers are also structurally similar (Sixma and Pronk, et al., 1991, Sixma and Kalk, et al., 1993, Merritt and Sarfaty, et al., 1994). There is also a high degree of immunological cross-reactivity between the two molecules (Svennerholm and Wickström, et al., 1986) despite the fact that the majority of antibodies are directed against structural features of assembled pentamers; a further indication of the structural similarity between the two molecules.

CT has been found to be an effective oral immunogen that gives rise to intestinal IgA responses directed mainly against the B subunit. Furthermore, oral administration of CTB alone has also been found to effectively stimulate similar responses and especially in humans, CTB has been found to be a strong immunogen in the absence of either the adjuvant or toxic effects of the holotoxin. These responses are associated with high-level although relatively short-term (ca. 6–9 months) protection against challenge or natural infection with *Vibrio cholerae* and a much longer-lasting immunological memory (Svennerholm and Sack, et al., 1982, Svennerholm and Gothefors, et al., 1984, Svennerholm and Jertborn, et al., 1984, Clemens and Sack, et al., 1990, Quiding and Nordström, et al., 1991).

Antitoxin antibodies appear to act synergistically in their protective action together with intestinal IgA antibodies directed against bacterial cell-associated antigens such as the lipopolysaccharide (LPS) of *V. cholerae* O1 (Svennerholm and Holmgren, 1976) or of the novel serotype O139 (J. Holmgren, et al., unpublished). Based on these findings an oral vaccine against cholera has been developed consisting of CTB together with killed whole cells of *V. cholerae* O1 (Holmgren and Svennerholm, et al., 1992) which has given rise to protection lasting several years (Clemens and Sack, et al., 1990) and which is presently being modified to also include cells of the O139 serotype.

Large-scale field trials of the B subunit-O1 whole cell vaccine in Bangladesh demonstrated in addition to the long-term protection observed against cholera, significant short-term cross-protection against ETEC infection due to the CTB component (Clemens and Sack, et al., 1988(a)). Such protection against ETEC afforded by the cholera vaccine was subsequently confirmed in a study of Finnish tourists travelling to Morocco (Peltola and Siitonen, et al., 1991). Based on this a more broad-spectrum vaccine against ETEC has been developed in which CTB is used in conjunction with killed *E. coli* expressing the major colonisation factor antigens involved in adhesion to the intestinal epithelium (Svennerholm and Århen, et al., 1991). The *E. coli* strains were included in order to provide immunity against ETEC strains releasing a heat-stable enterotoxin (STa) either alone or together with LT.

In areas where both cholera and ETEC are endemic it would be desirable to have a single vaccine that could effectively protect against both infections. This could in part be achieved by increasing the protection against ETEC afforded by the CTB component of the already licensed cholera vaccine. Although LTB and CTB show significant immunological cross-reactivity, neutralisation of LT by serum from CTB-immunised individuals is not as effective as the same serum is in neutralising CT (Åhren and Wenner as, et al., 1993). Conversely, it is known that antisera against LT or LTB react in higher titre with LT than with CT (Svennerholm and Holmgren, et al., 1983). It is therefore possible that some neutralising epitopes in LTB are absent in CTB and vice versa. This is further indicated by the identification of LTB-specific neutralising antibodies (Svennerholm and Wickström, et al., 1986).

The inclusion of CTB in both the cholera and ETEC vaccines has led to the development of an expression system for the overproduction of recombinant protein that can be produced in large quantities and in the total absence of the toxic CTA subunit (Sanchez and Holmgren, 1989, Lebens and Johansson, et al., 1993). This has also opened the way to relatively simple procedures for the genetic modification of CTB such as the generation of protein fusions carrying foreign peptide antigens.

The present invention is based on modification by site-directed mutagenesis of the structural gene coding for CTB resulting in hybrid proteins in which LTB-specific epitopes were introduced into proteins that remained essentially CTB. thereby generating such hybrid molecules carrying LTB-specific epitopes in addition to cross-reactive and CTB-specific ones, in order to increase the immunological cross-reactivity. Such hybrid CTB/LTB molecules have been developed in order to provide a broad spectrum vaccine for the prevention or treatment of enterotoxigenic illness.

DESCRIPTION OF THE INVENTION

The present invention is, in one aspect, directed to a hybrid molecule between heat-labile enterotoxin B subunit (LTB)[SEQ ID NO: 2] and FIG. 1 and cholera toxin B subunit (CTB)[SEQ ID NO: 1] and FIG. 1, which molecule comprises an amino-acid sequence which is composed of the amino-acid sequence of mature CTB[SEQ ID NO: 5] and identified in FIG. 1 as resided +1 to +103 in which such amino-acid residues are substituted with the corresponding amino-acid residues of mature LTB[SEQ ID NO: 6] and identified in FIG. 1 as resides +1 to +103 which impart LTB-specific epitope characteristics to said immunogenic mature CTB, or vice versa.

Thus, said hybrid molecule may alternatively comprise an amino-acid sequence which is composed of the amino-acid sequence of mature LTB in which such amino-acid residues are substituted with the corresponding amino-acid residues of mature CTB which impart CTB-specific epitope characteristics to said immunogenic mature LTB.

In a preferred embodiment said hybrid molecule of the invention has an amino-acid sequence which is composed of the amino-acid sequence of mature CTB in which the amino-acid residues identified in FIG. 1 in positions 1, 94 and 95 are substituted with the corresponding amino-acid residues of LTB.

In another preferred embodiment said hybrid molecule of the invention has an amino-acid sequence which is composed of the amino-acid sequence of mature CTB in which the amino-acid residues identified in FIG. 1 in positions 1–25 are substituted with the corresponding amino-acid residues of LTB.

The amino-acid sequences of mature CTB and mature LTB are depicted in FIG. 1 and start with the amino acid +1. Corresponding structural genes are depicted in the same Figure.

Another aspect of the invention is directed to a structural gene coding for a hybrid molecule according to the invention. Further, the invention is directed to a plasmid containing such a structural gene.

Yet another aspect of the invention is directed to an immunogenic protein which comprises a hybrid molecule according to the invention.

In an embodiment of this aspect of the invention said immunogenic protein is a fusion protein of said hybrid molecule of the invention and an immunoreactive amino-acid sequence of or from a prokaryotic or eukaryotic cell or a virus.

Still another aspect of the invention is directed to a vaccine which comprises as an immunising component an immunologically effective amount of an immunogenic protein according to the invention. Preferably said vaccine is against enterotoxin-induced illness, such as diarrhoea.

The B subunit hybrid of the invention is intended for use in a method of preventing or treating enterotoxin-induced illness in an individual (animal or human being) comprising administration to said individual of an immunologically effective amount of an immunogenic protein according to the invention.

DESCRIPTION OF THE DRAWINGS

FIG. 1. Comparison between the sequences of LTB from a human ETEC isolate (Leong, et al., 1985) and CTB (M. Lebens, unpublished). For differences resulting in amino acid changes, the residue at the corresponding position of LTB is given above the DNA sequence. Numbers below the CTB amino acid sequence indicate the position of amino acid residues in the mature CTB and LTB proteins.

FIG. 2a) pML-LCTBtacA was generated by insertion of a gene in which the SacI/AccI fragment from pML-LCTBtac1 (21) was replaced by synthetic oligonucleotides encoding the first 25 amino acids of LTB. The remainder of the ctxB gene was unaltered. The plasmid carries the LTB signal peptide and ribosome binding sequences. FIG. 2b) pML-LCTBtacB was generated from pML-CTBtac by PCR-directed mutagenesis in which a unique EcoRI site was introduced and the amino acids at positions 94 and 95 were altered to correspond to the same position in LTB. The plasmid carries the CTB signal peptide and the lamda cII ribosome binding sequence. Altered sequences are shown in boxes. Sequences depict only the relevant regions of the hybrid genes.

PREPARATION OF HYBRID CTB/LTB MOLECULES OF THE INVENTION

The hybrid CTB/LTB molecules of the invention may be prepared according to any known method in the art of producing peptides and proteins, such as genetic engineering and/or peptide synthesis, e.g. according to Merrifield. To illustrate the preparation of such molecules, two hybrid CTB/LTB molecules of the invention were prepared as follows.

Generation of hybrid CTB/LTB molecules.

Figure 2A:
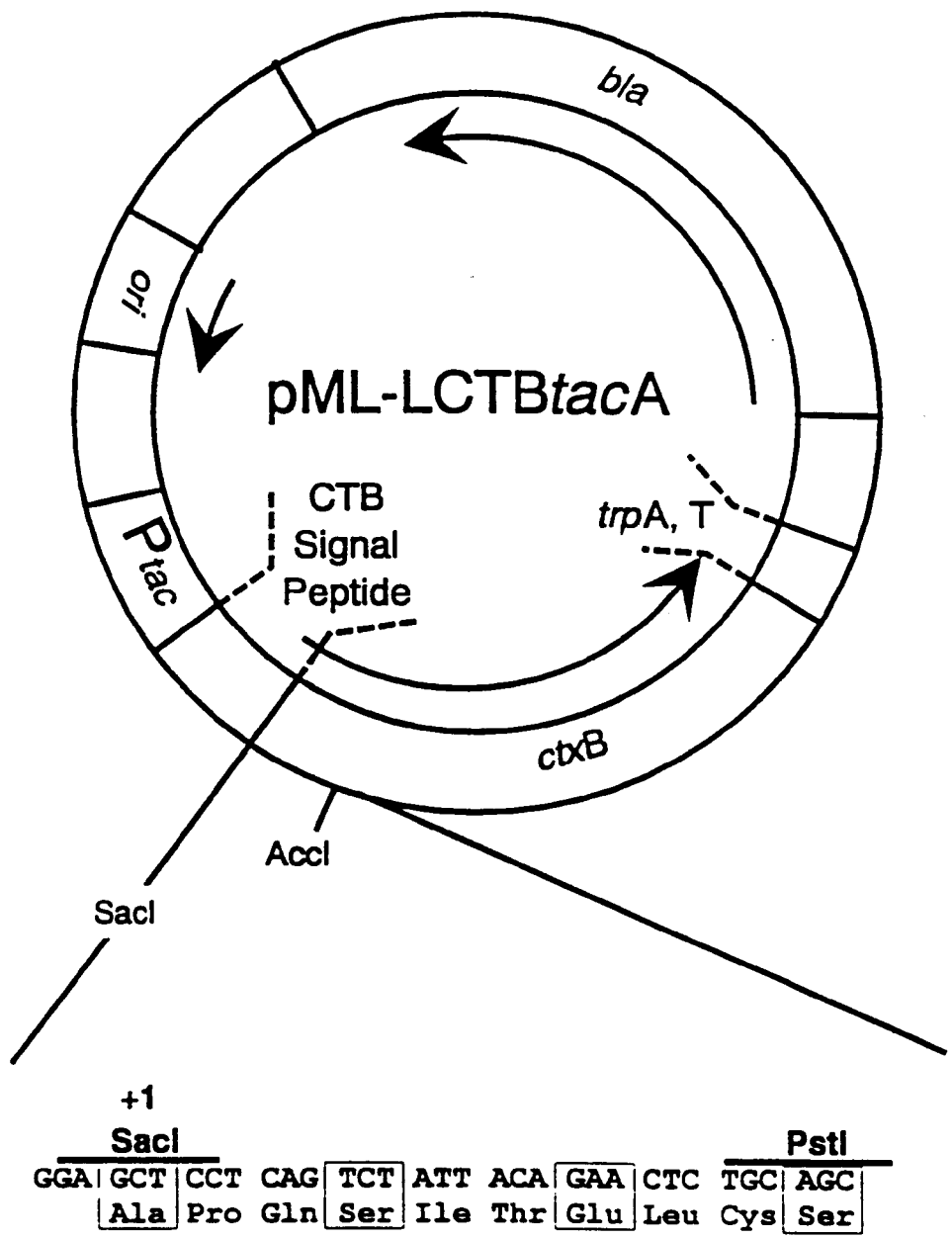
FIGS. 2a and 2b Plasmids encoding CTB/LTB hybrids. In both plasmids the ctxB derived genes are expressed from the tac promoter.
Figure 2B:
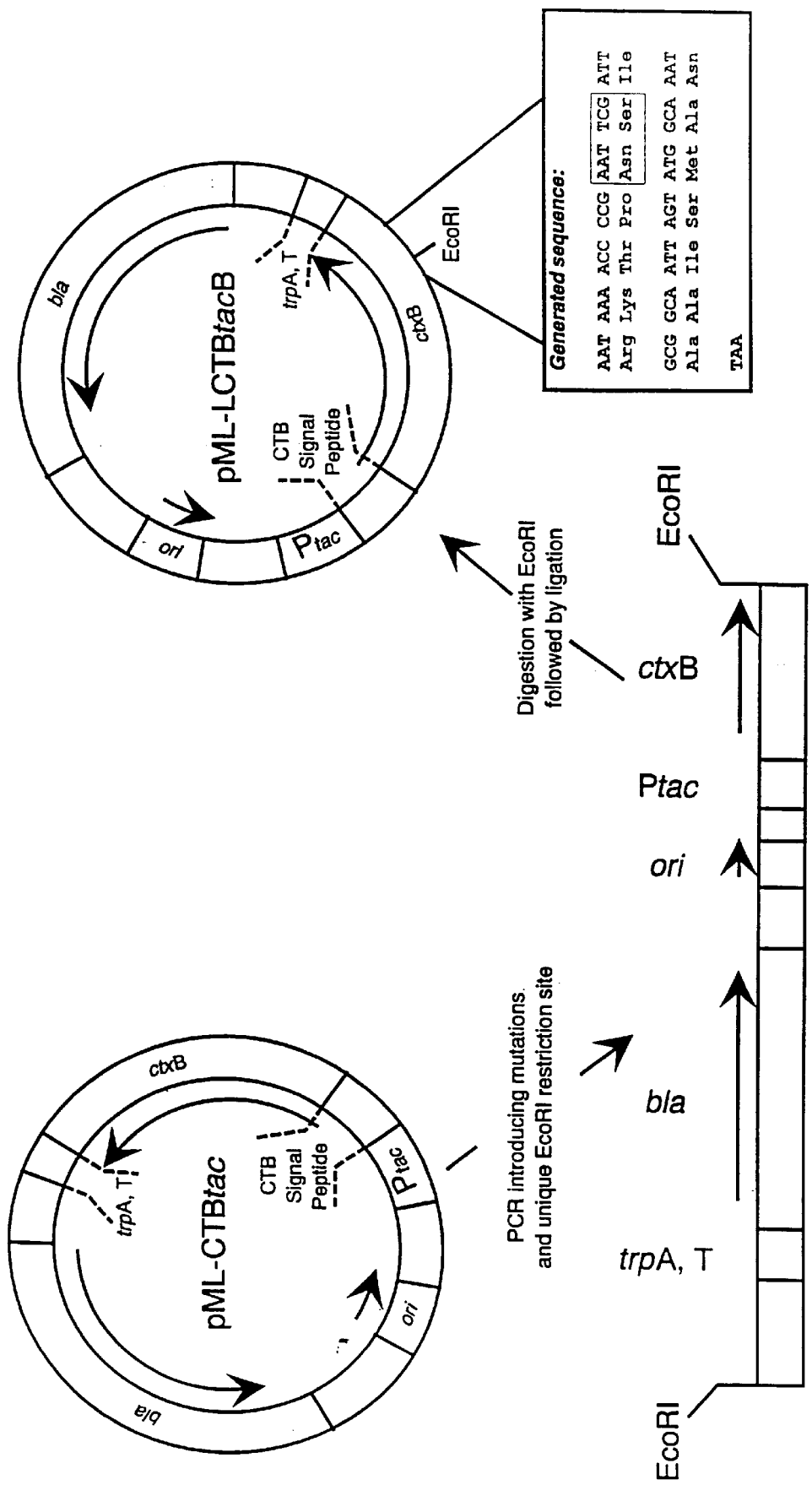

The two hybrid toxin genes used in the present invention were generated from two different CTB expression vectors. In the first, modifications were achieved by the insertion of synthetic oligonucleotides between convenient restriction sites within the ctxB gene and in the second, mutations were generated by the use of specific primers in the PCR amplification of entire plasmid as previously described (Schödel and Milich, et al., 1991). The two resulting plasmids were pML-LCTBtacA and pML-LCTBtacB carrying modified ctxB genes the sequences of which were confirmed by DNA sequencing and are indicated in FIG. 2. The hybrid protein LCTBA expressed by pML-LCTBtacA is identical to LTB in it's first 25 amino acids and thereafter was identical to CTB. That expressed by pML-LCTBtacB and designated LCTBB and is altered to correspond to LTB at positions 1, 94 and 95 but is otherwise identical to native CTB from classical O1 V. cholerae strain 395.

The hybrid proteins were expressed in V. cholerae strain JS1569 resulting in accumulation of the products in the growth medium from which they could be purified by hexametaphosphate precipitation followed by HPLC.

The proteins appeared on the basis of SDS PAGE to be identical to the control CTB protein in the case of LCTBA but in the case of LCTBB to run more like LTB, particularly in the monomeric form.

Antigenic analysis of CTB/LTB hybrids.

The two hybrid proteins were partially purified from the growth medium of V. cholerae carrying the respective expression vectors and subjected to a variety of different assays in order to determine their antigenic properties in comparison with native CTB and LTB.

Initially fixed concentrations of the different proteins were titrated with different CTB- or LTB-specific antibodies in GM1-ELISA. The method would measure affinity differences for either or both the GM1 receptor and the different detecting antibodies, but we have previously shown that the different proteins bind identically to GM1 and that the differences were therefore antibody-specific (results not shown). The results are shown in table 1. It can be seen that the profile of the titres obtained for a range of both monoclonal antibodies and adsorbed polyclonal antisera can differ between hybrid and native proteins. The results indicate that the hybrid protein LCTBA has acquired LTB-specific epitopes that can be recognised on the basis of reactions with monoclonal antibodies; notably epitopes recognised by the LTB-specific monoclonal antibodies LT33:8 and LT80:7. It still reacts however with the CTB-specific antibody CTWi. This was also demonstrated in western blots.

In the case of LCTBB none of the monoclonal antibodies used demonstrated any changes in the antigenicity of the hybrid molecule. There are two possible explanations for this; one is that the relatively small number of changes in the molecule required screening with a larger range of antibodies in order to find one that would demonstrate an affinity for the particular epitope. Alternatively, assays based on GM1-ELISA may not detect changes in the region of the molecule that are hidden within the GM1 binding site.

Immunisations with hybrid proteins give rise to cross-reactive antisera

Following immunisation with either LTB, CTB or the different hybrid molecules, resulting sera were analysed for levels of overall antibodies against LTB and CTB and subsequently for levels of LTB-specific antibodies.

Figure 3:
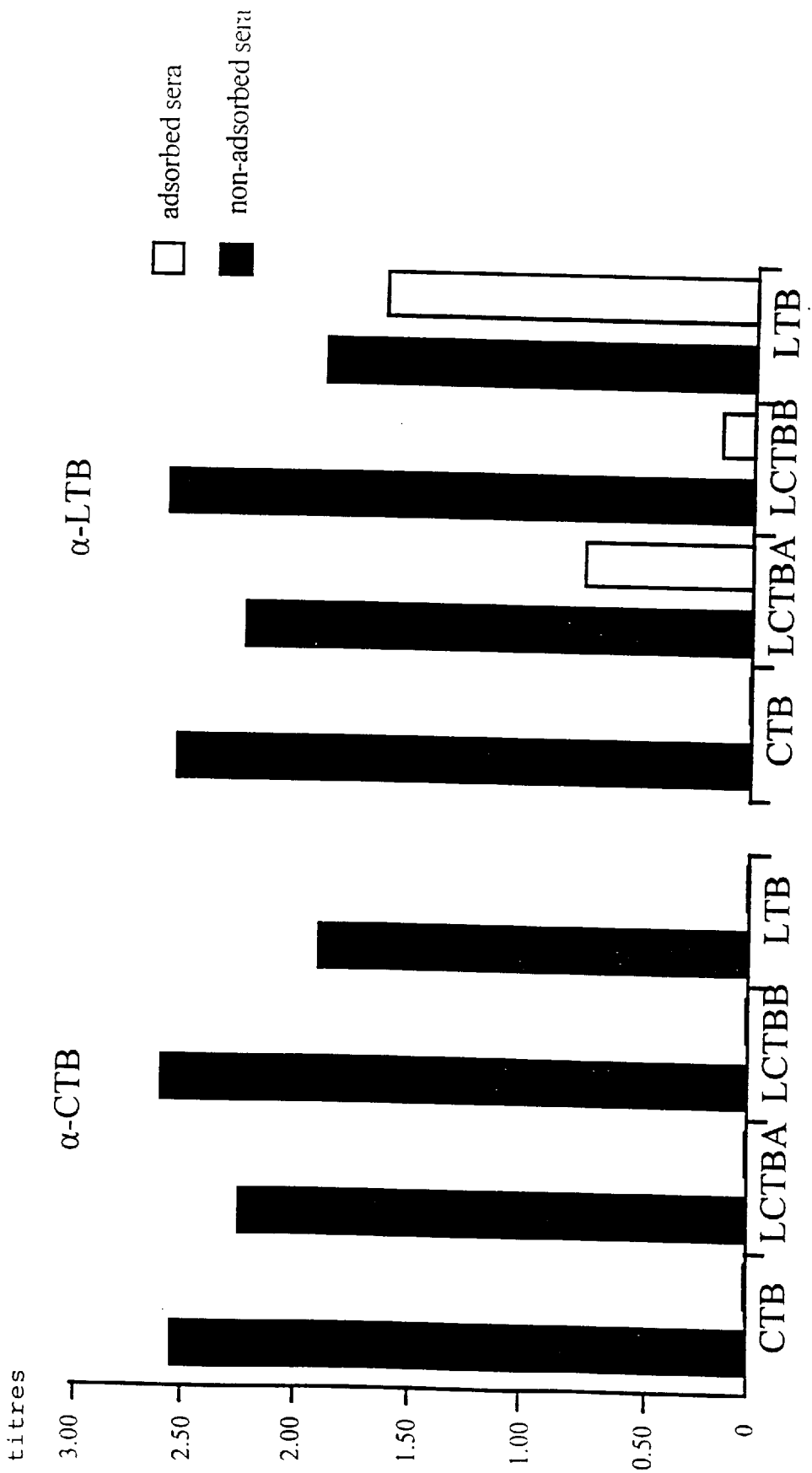
FIG. 3. IgG antibody response to ip immunisation with either rCTB, rLTB, or the CTB/LTB hybrid proteins LCTBA (A) or LCTBB (B) after each of the three immunisations (groups 1,2 and 3) respectively. Titres are the means of two mice and were determined by GM1-ELISA as described in the Materials and Methods.

FIG. 3 shows the levels of antibodies against CTB and LTB after each of the three immunisations. Prior to the first immunisation there were no detectable titres against either B subunit in any of the mice tested. In the cases of CTB and both of the hybrid proteins the titres against CTB were consistently higher than those against LTB. In the mice immunised with LTB the situation was reversed. In mice immunised with CTB or the LCTBB hybrid molecule there were no significant differences between the relative titres obtained against CTB and LTB after the first and second immunisations. In both cases the CTB titre was clearly higher than that against LTB. In mice immunised with LCTBA however, the levels of titres against LTB and CTB were more similar to each other. This was due to an elevated level of anti-LTB antibodies and a depressed level of anti-CTB antibodies in comparison with the CTB- and LCTBB-immunised mice. After the third immunisation it can be seen that in both groups of mice immunised with the hybrid molecules the anti-CTB titres are similar to those in mice immunised with CTB but that the anti-LTB levels are higher.

Figure 4:
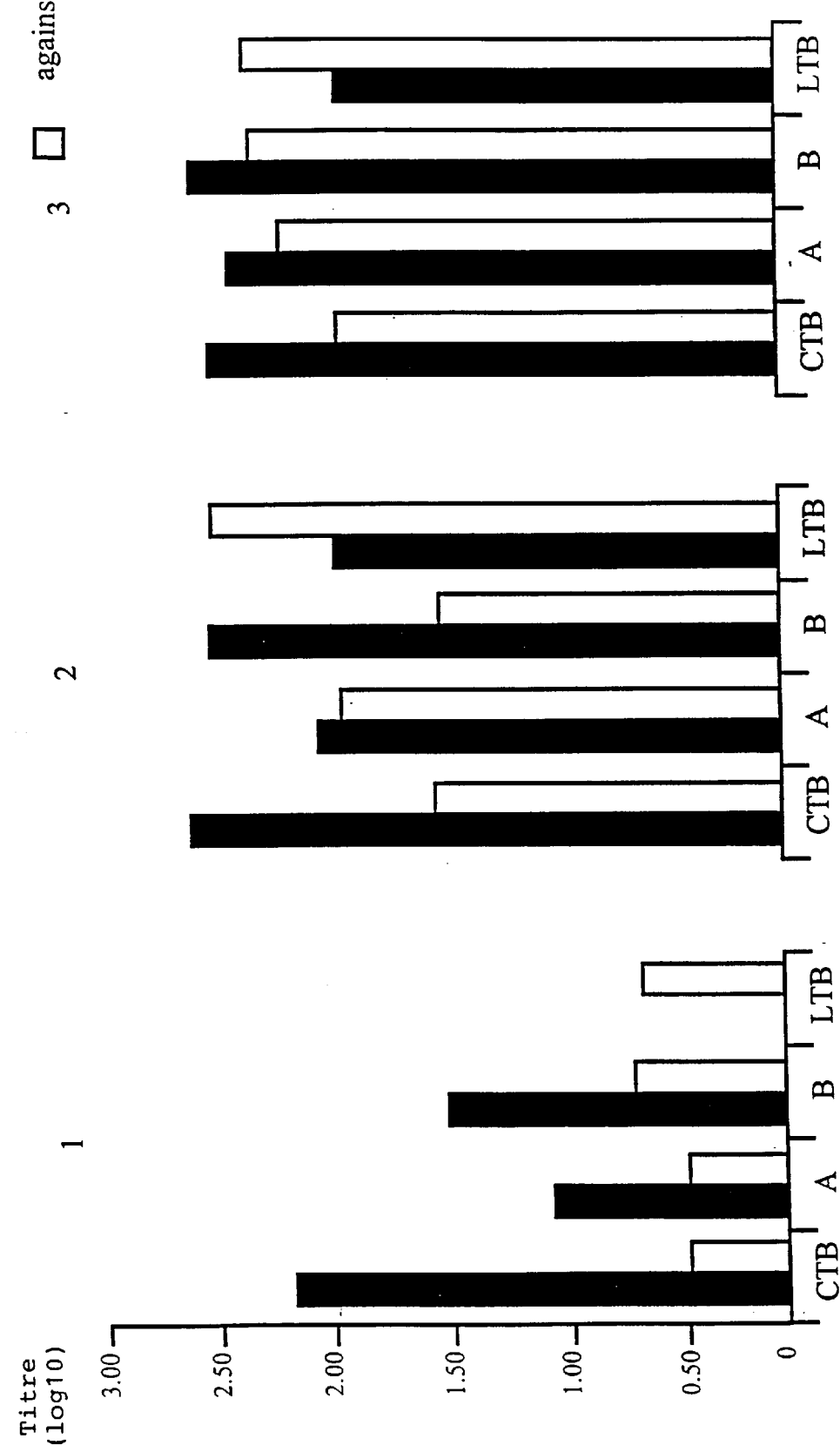
FIG. 4. Effect of absorption with CTB on titres of CTB- and LTB-reactive antibodies in sera of mice obtained after three immunisations with either rCTB, rLTB or the CTB/LTB hybrid proteins LCTBA or LCTBB.

When testing whole sera for titres of antibodies against LTB or CTB the issue is clouded by the presence of cross-reactive antibodies. In order to determine whether the differences observed in the different sera were due to changes in the levels of LTB-specific antibodies, the sera taken after the third immunisation were adsorbed with CTB-Sepharose to remove both cross-reactive and CTB-specific antibodies. They were then assayed for anti-CTB and anti-LTB titres. The results are shown in FIG. 4. It can be seen that the treatment effectively removes all anti-CTB antibodies from the sera. In mice immunised with CTB the entire observed anti-LTB titre is due to cross-reactive antibodies and no LTB reactive antibodies remain after adsorption. In the case of both LCTBA and LCTBB significant anti-LTB titres remain, although these are not as high as in mice immunised with LTB. It is evident that the mutations introduced into the CTB molecule do have an immunological effect giving rise to LTB-specific antibodies. It is also clear that in LCTBA where there were seven substitutions in the CTB molecule the effect is greater than in LCTBB where there are only three.

Neutralisation of CT and LT by different B subunit antisera.

The different antisera were tested in an in vitro assay for their ability to neutralise either LT or CT. The results are shown in Table 2. Under the conditions used in the assay CTB and LTB antisera are only slightly cross-reactive. LTB antiserum did not neutralise CT at any dilution within the range used whereas CTB antiserum had a slight effect on LT. In contrast, antisera to either of the hybrid molecules had significant neutralising activity against both CT and LT. Even after complete absorption of the CT neutralising activity of the antisera with CTB there was still significant LT neutralising activity. These results indicate that the substitutions made within the CTB molecule introduce neutralising LTB epitopes whilst at the same time retaining CT neutralisation epitopes. It is significant that the level of neutralising activity demonstrated against LT by antiserum from mice immunised with LCTBB is almost comparable to that found for serum from LCTBA-immunised mice despite the presence of only low levels of LTB-specific antibodies as tested with GM1 ELISA. This suggests that the amino acids at positions 94 and 95 of the B subunit structure form part of a powerful neutralising epitope that might be located at or near the recepto-binding site.

Summary of the results presented in the experimental part of the specification

The presented work describes the synthesis and analysis of two hybrid B subunit toxin molecules essentially composed of CTB, in which mutations have altered specific amino acid residues to resemble the corresponding positions in human LTB. The two proteins were found to be expressed at high levels and to retain the essential characteristics of both CTB and LTB. Both assembled into pentamers and both bound to GM1 ganglioside. In addition both molecules reacted similarly to the wild type CTB and LTB with the cross-reacting monoclonal antibody LT39 and also reacted strongly with polyclonal antisera to either CTB or LTB. In reactions with other LTB- or CTB-specific monoclonal antibodies, however, distinctions between the different proteins could be made that suggested that the novel proteins did indeed carry epitopes specific to each of the wild-type proteins on the same molecule. This was further illustrated by immunisation experiments which demonstrated an increased cross-reactivity of sera obtained from animals immunised with the hybrid proteins. It was demonstrated that in the CHO cell toxin-neutralisation assay antisera to the hybrid molecules neutralised LT more effectively than did antiserum to CTB alone, and that this activity could not be absorbed away by CTB.

The two hybrid molecules used in the present work were generated to illustrate the effect of mutations at distinct regions of the CTB molecule. In the first construct the amino terminus of CTB was altered whereas in the second, two residues were changed at a locus close to the carboxy terminus thought to be involved in the substrate specificity of receptor binding. The mutation Thr→Ala at position 1 of LCTBB was not investigated in the present work. The recombinant CTB used for controls was produced from an expression system described previously (Lebens and Johansson, et al., 1993). The control recombinant carried the Thr→Ala mutation at position 1 which we have previously shown to have no immunological significance (Lebens and Johansson, et al., 1993 and M. Lebens and J. Holmgren, unpublished data).

From the results it is clear that the more extensive alteration at the amino terminus of CTB gives rise to more LTB-specific antibodies (as defined by GM1-ELISA antibody titres that are not absorbed away by CTB-Sepharose) compared to the two residue change at positions 94 and 95 of the mature protein which gave detectable but very low anti-LTB specific GM1 -ELISA titres. Of considerable interest therefore, was the finding that neutralisation of LT (and CT) by antisera to the two mutant B subunits in the CHO cell was similar. This suggests that despite the apparent lower titre of LTB-specific antibodies generated by the second hybrid, the antibodies have an equivalent neutralising effect indicating that the two residues affected lie within a neutralising epitope. It is further evident that there are more than one such neutralising epitopes on the B subunit molecules since neither mutant loses the ability to neutralise CT despite the likelihood that some CTB-specific neutralising epitopes may have been lost as a result of the substitutions.

The cross-reactivity of the mutant CTB molecules could be attributed to the specific changes generated since these gave rise to LTB-specific antibodies unaffected by immunosorbent removal CTB-specific as well as all cross-reactive antibodies resulting in the complete loss of CT-neutralising activity in the CHO cell assay. The LT-neutralising activity however, was retained.

From these investigations it is clear that hybrid molecules containing both CTB- and LTB-specific neutralising epitopes can be generated. In addition, the recently described over-expression system for CTB allows these proteins to be produced in large quantities. Thus such molecules are now provided for the incorporation thereof either into separate cholera and ETEC vaccines or into a single broad-spectrum vaccine designed to give significant protection against both types of diarrhoeal disease.

MATERIALS AND METHODS

Bacterial strains and plasmids

The bacterial strains used in the present work for the production of recombinant CTB (rCTB) and LTB (rLTB) and mutant derivatives were the O1 El Tor *V. cholerae* strain JBK70 (Kaper and Lockman, et al., 1984), and the O1 Classical *V. cholerae* strain JS1569 (Lebens and Johansson, et al., 1993). Strains carrying the appropriate recombinant plasmids were stored frozen in medium with 20% glycerol at −70° C. Cultures were revived by streaking each strain onto L-agar supplemented with ampicillin 100 μg/ml.

Plasmids generated in the present study are shown in FIG. 2.

DNA manipulation

Manipulation of DNA including plasmid preparation, use of restriction enzymes, DNA ligation and agarose gel electrophoresis were done according to standard procedures essentially as described by Sambrook and Fritsch, et a/. (1989). Restriction enzymes were used in the buffers supplied by the manufacturers. Oligonucleotides for insertion into plasmids by ligation or for amplification using PCR were obtained from Innovagen AB, Sweden.

PCR was used to introduce mutations into a plasmid-borne ctxB gene according to the method described by Sch ödel and Milich, et al. (1991). DNA sequencing was done using the Sequenase version 2.0 kit obtained from Amersham (UK).

Preparation of CTB and LTB and their mutant derivatives

Crude rCTB and its derivatives were prepared from strain *V. cholerae* JS1569 carrying the relevant expression plasmid. LTB was prepared from *V. cholerae* strain JBK70 carrying the expression plasmid pMMB68 (Sandqvist and Hirst, et al., 1987).

Cultures were grown on modified syncase (Lebens and Johansson, et al., 1993) and the CTB or LTB accumulated in the medium was recovered by hexametaphosphate precipitation as described previously (Lebens and Johansson, et al., 1993). The concentration of the B subunit obtained was determined by GM1-ELISA (Svennerholm and Holmgren, 1978) using the cross-reactive monoclonal antibody LT39.

A method for further purification of LTB and CTB derivatives was developed using HPLC. Hexametaphosphate precipitates were resuspended in 20 mM Tris-HCl pH 9. The resulting suspension was then centrifuged at 10,000 rpm for 3 minutes and the supernatant containing the B subunit was filtered through a 0.2 m sterile filter. HPLC was performed on a Waters 600 Multisolvent Delivery System (Millipore Corp., USA) using a DEAE Mem-Sep HP1000 column (Millipore Corp., USA). The B subunits were first bound to the column at pH 9 (20 mM Tris-HCl ) and eluted from the column with 0.16M (for LCTBA) or 0.18M (for LCTBB) sodium acetate at pH 8.

In vitro antigenicity and protein analysis

Wells of polystyrene ELISA plates were coated with 100 μl of 0.3 nmol/ml GM1 ganglioside for 6 hours at room temperature and kept at 4° C. until use. Coated plates were first washed with two changes of PBS and blocked with phosphate buffered saline, pH 7.2 (PBS), 0.1% (w/v) bovine serum albumin (BSA) for 30 minutes at 37° C. Solutions of 25 ng/ml of each B subunit preparation were obtained by diluting concentrated stock solutions in PBS, 0.1% BSA. 100 ml aliquots of these diluted samples were used to coat the blocked plates by incubation for 1 h at room temperature.

Different antibody solutions were then added to the first row of the plates and titrated out with five-fold serial dilutions. The antibodies bound to the B subunits were then detected with a secondary anti-mouse or anti-rabbit immunoglobulin conjugated with horseradish peroxidase (HRP) (Jackson, Pa., USA). After incubation for 1 h at room temperature, the binding of the antibodies was detected using the chromogenic substrate o-phenylenediamine (OPD) and $H_2O_2$ in citrate buffer (pH 4.5) as described previously (Svennerholm and Holmgren. 1978). The plates were washed three times with PBS, 0.05% Tween between each step. Titres were determined as the reciprocal dilution giving an absorbance at 450 nm of 0.4 above background after a reaction time of 10 min.

SDS-polyacrylamide electrophoresis and electotransfer of resolved proteins to nitrocellulose was done using the mini protean II apparatus obtained from Biorad (CA, USA) under conditions recommended by the manufacturers.

Mouse immunisations

Pairs of C57/Black mice were immunised three times intraperitoneally with either CTB, LTB or the mutant CTB derivatives. The first two doses contained 10 mg B subunit administered in 200 ml containing Freunds incomplete adjuvant and were given ten days apart. The third dose of 20 mg B subunit was given without any adjuvant fourteen days after the second dose. The mice were bled prior to the first two doses and sacrificed seven days after the third dose after which blood was collected for analysis. Sera were prepared and stored at −20° C. until used.

Serum titre determination

Sera obtained from immunisations were tested by GM1-ELISA (Svennerholm and Holmgren, 1978). Immediately before use GM1 coated plates were first washed twice with PBS and blocked with PBS, 0.1% BSA at 37° C. for 30 minutes. The plates were then divided into two groups. 100 μl of CTB 0.5 μg/ml in PBS, 0.1% BSA was added to the wells of the first group of plates and 100 μl of LTB 0.5 μg/ml in PBS, 0.1% BSA was added to the wells of the second group. The plates were then incubated at room temperature for 1 h and washed three times with PBS, 0.05% Tween. 100 μl of a solution of PBS, 0.1% BSA, 0.05%Tween was then added to all the wells except those in the first row. To wells in the first row 150 ml aliquots of 1/1000 dilutions of the sera in PBS, 0.1% BSA were added. These were then titrated out with serial three-fold dilutions and incubated at room temperature for 1 h. After three washes with PBS, 0.05% Tween, antibodies bound to CTB and LTB were assayed by incubation with anti-mouse IgG conjugated with HRP (Jackson, Pa., USA). The chromogenic substrate was OPD and titres were calculated in the same manner as for the determination of in vitro antigenicity described above.

CTB antibody absorption

Sera were absorbed with CTB-Sepharose beads in order to remove both CTB-specific antibodies and antibodies that would cross-react with LTB. CTB-Sepharose was prepared by covalently linking CTB pentamers to cyanogen bromide-activated Sepharose (Pharmacia AB, Sweden) according to the manufacturers instructions.

The sera were first diluted 1:10 in PBS. 100 μl of this dilution was incubated in a micro centrifuge tube with 50 μl of Sepharose-CTB beads with intermittent shaking for 1 hour at room temperature. They were then centrifuged at 9000 rpm in a bench top micro centrifuge for 2 minutes and the supernatant was recovered. The procedure was then repeated. Absorbed sera were assayed against CTB and LTB by GM1-ELISA as described above.

Toxin neutralisation tests

Sera obtained after the third immunisation of mice with the various CTB derivatives and LTB were tested in a Chinese Hamster Ovary (CHO) cell assay (Guerrant and Brunton, et al., 1974) for their ability to inhibit the toxicity of CT or LT before and after adsorption with CTB-Sepharose. Unabsorbed sera was first diluted 1:20. 50 ml aliquots of the resulting sera were then serially diluted in duplicate in micro titre plates with 3-fold dilutions. To the first group of duplicate wells was added 0.2 ng CT in 50 μl HAM F12 medium containing 1% BSA and to the second group was added a solution of LT in the same medium. The plates were incubated for 1 h at room temperature after which 100 μl of a suspension of $2 \times 10^5$ cells/ml in F12 HAM medium was added to all the wells. The incubation was allowed to proceed for 1 h at 37° C. in a 10% $CO_2$, 5% $O2$ atmosphere. The cells were fixed with methanol and stained with Giemsa solution (Merck). The cells were observed for damage by light microscopy. The same procedure was applied to the sera after they were absorbed with CTB-Sepharose beads. All experiments were done in duplicate.

REFERENCES (a) Clemens, J., Sack, D., Harris, J. R. J., Chakraborty, J., Neogy, P. K., Stanton, B., Huda, N., Khan, M. U., Kay, B. A., Khan, M. R., Ansaruzzaman, M., Yunus, M., Rao, M. R., Svennerholm A.-M. and Holmgren, J. (1988) *J. Infect. Dis.* 158, 372–377.

(b) Clemens, J., Sack, D., Harris, J. R. J., van Loon, F., Chakraborty, J., Ahmed, F., Rao, M. R., Khan, M. R., Yunus, M., Huda, N., Stanton, B., Kay, B. A., Walter, S., Eeckels, R., Svennerholm A. -M. and Holmgren, J. (1990) *Lancet* i, 270–273.

Guerrant, R. L.; Brunton, L. L.; Schnaitman, R. C.; Rebhun; L. I.; and Gliman, A. G. (1974) *Infect. Immun.* 10, 320–327

Holmgren, J. (1981) *Nature* 292, 413–417.

Holmgren, J., Fredman, P., Lindblad, M., Svennerholm, A. -M. and Svennerholm, L. (1982) *Infect. Immun.* 38, 424–433.

Holmgren, J., Svennerholm, A. -M.; Jertborn, M.; Clemens, J.; Sack, D. A.; Salenstedt, R. and Wigzell, H. (1992) *Vaccine* 10, 911–914.

Quiding, M., Nordström, I., Kilander, A., Andersson, G., Hanson L. -Å., Holmgren, J. and Czerkinsky C. (1991) *J. Clin. Invest.* 88, 143–148.

Kaper, J. B., Lockman, H., Baldini, M. M. and Levine, M. M. (1984) *Nature* 308, 655–658.

Lebens, M., Johansson, S., Osek, J., Lindblad, M., and Holmgren; J. (1993) *BioTechnology* 11, 1574–1578.

Leong, J., Vinal, A. C. and Dallas, W. S. 1(985) *Infect. Immun.* 48, 73–78.

Merrit, E. A., Sarfaty, S., van den Akker, F., L'Hoir, C., Martial, J. A., and Hol, W. G. J. (1994) *Prot. Sci.* 3, 166–175.

Peltola, H., Siitonen, A., Kyrönseppä, H., Simula, I., Mattila, L., Oksanen, P., Kataja, M. J. and Cadoz, M. (1991) *Lancet* 338, 1285–1289.

Sambrook, J., Fritsch, E. F. and maniatis, T. (1989) Molecular cloning. A laboratory manual (2nd ed.) Cold Spring Harbor Laboratory Press, Cold Spring Harbor, N.Y.

Sanchez, J., and Holmgren, J. (1989) *Proc. Natl. Acad. Sci USA* 86, 481–485.

Sandkvist, M., Hirst, T. and Bagdasarian, M. (1987) *J. Bacteriol.* 169, 4570–4576.

Schödel, F., Milich, D. R., and Will, H. 1991) In Brown, F., Chanock, R. M., ginsberg, H. S and Lerner, R. A. (eds), *Vaccines* 91, Cold Spring Harbor Laboratory Press, Cold Spring Harbor, N.Y. pp319–325.

Sixma, T. K., Kalk, K. H., van Zanten, B. A. M., Dauter, Z., Kingma, J., Witholt, B. and Hol, W. G. J. (1993) *J Mol. Biol.* 230, 890–918.

Sixma, T. K., Pronk, S. E., Kalk, K. H., Wartner, E. S., van Zanten, B. A. M., Witholt, B. and Hol, W. G. J. (1991) *Nature* 351, 371–378.

Spangler, B. D. (1992) *Microbiol. Rev.* 56, 622–647.

Svennerholm, A. -M., Gothefors, L., Sack, D. A., Bardhan, P. K. and Holmgren J. (1984) *Bull. WHO.* 62, 909–918.

Svennerholm, A. -M. and Holmgren, J. (1976) *Infect. immun.* 13, 735–740.

Svennerholm A. -M. and Holmgren, J. (1978) *Curr. Microbiol.* 1, 19–23.

Svennerholm, A. -M., Holmgren, J., Black, R., Levine, M. and Merson. M. M. (1983) *Infect. Dis.* 147, 514–522.

Svennerholm, A. -M., Jertborn, M., Gothefors, L., Karim, A. M. M. M., Sack, D. A., and Holmgren J. (1984) *J. Infect. Dis.* 149, 884–893.

Svennerholm, A. -M., Wickström, M., Lindblad, M., and Holmgren, J. (1986) *Med. Bio.* 64, 23–30.

Svennerholm, A. -M., Sack, D. A., Holmgren J. and Bardhan, P. K. (1982) *Lancet* i, 305–308.

Svennerholm, A. -M., Åhren, C., Wennerås, C. and Holmgren, J. (1991) In Wadström, T., Mekele, H., Svennerholm, A. -M., and Wolf-Watz, H. (eds) *Molecular pathogenesis of gastrointestinal infections* Plenum, London. pp. 287–294.

Åhrén, C., Wennerås, C., holmgren, J. and Svennerholm, A. -M. (1993) *Vaccine* 11, 929–935.

TABLE 1

Generation of LTB-specific epitopes with retention of CTB epitopes in hybrid proteins.

| Antibody tested | log₁₀ antibody titre[a] to | | | |
|---|---|---|---|---|
| | rCTB | LCTBA | LCTBB | LTB |
| Monoclonal antibodies | | | | |
| LT39 | 4.3 | 4.4 | 4.1 | 4.1 |
| LT33:8 | 0 | 4.3 | 0 | 4.2 |
| LT80:7 | 0 | 3.3 | 0 | 3.9 |
| CTWi | 3.4 | 2.8 | 3.0 | 0 |
| Polyclonal antiserum | | | | |
| R953 | 4.5 | 3.9 | 4.4 | 4.9 |
| R953abs | 2.2 | 3.1 | 1.6 | 4.4 |

[a] Antibody titres were determined by a GM1-ELISA procedure (see Materials and Methods). LT39 is a cross-reactive monoclonal antibody reacting similarly with both LTB and CTB. LT33:8 and LT80:7 are LTB specific monoclonal antibodies and CTWi is a CTB-specific monoclonal antibody. R953 is a rabbit polyclonal hyperimmune serum raised against LTB and R953abs is the same serum after absorption with CTB. Estimated titre differences exceeding $\log_{10}=0.5$ (i.e. 3-fold) are considered to be significant.

TABLE 2

Hybrid proteins give rise to antisera with increased LT-neutralising activity.

| Immunisation with | Neutralisation titre[a] | | | |
|---|---|---|---|---|
| | non-absorbed serum | | absorbed serum | |
| | CT | LT | CT | LT |
| CTB | 180 | <20–20 | <20 | <20 |
| LCTBA | 60 | 60 | <20 | 80 |
| LCTBB | 60 | 60–180 | <20 | 20–40 |
| LTB | <20 | 60–180 | <20 | 40–80 |

[a] Neutralization of LT and CT by sera obtained after three immunizations of mice with CTB, LTB or either of the two LTB/CTB hybrids was determined using a CHO cell assay (see Materials and Methods). The sera were also absorbed with CTB-Sepharose and assayed by the same procedure. Experiments were conducted such that the starting concentrations in the first wells were equivalent in experiments with sera before and after absorption with CTB-Sepharose. In order to achieve this unabsorbed sera were diluted 1:20 in the first well whereas following absorption they were used undiluted. Unabsorbed sera were serially diluted with three-fold dilutions and absorbed sera were serially diluted with two-fold dilutions. Displayed titres indicate the maximum dilution at which sera protected cells from damage and indicate the range obtained from titrations performed in two separate duplicated experiments.

We claim:

1. A hybrid protein molecule consisting of heat-labile enterotoxin B subunit (LTB) and cholera toxin B subunit (CTB), which comprises an amino acid sequence which is composed of
   (a) the amino acid sequence of mature CTB as shown in FIG. 1 in which amino acid residues are substituted with corresponding amino acid residues of mature LTB as shown in FIG. 1 which impart LTB-specific epitope characteristics to said immunogenic mature CTB; or
   (b) the amino acid sequence of mature CTB as shown in FIG. 1 in which amino acid residues are substituted with corresponding amino acid residues of mature LTB as shown in FIG. 1 which impart LTB-specific epitope characteristics to said immunogenic mature CTB.

2. The hybrid protein molecule according to claim 1, wherein said amino acid sequence is composed of the amino acid sequence of mature CTB in which amino acid residues in positions 1, 94 and 95 as shown in FIG. 1 are substituted with the corresponding amino acid residues of LTB as shown in FIG. 1.

3. The hybrid protein molecule according to claim 1, wherein said amino acid sequence is composed of the amino acid sequence of mature CTB in which amino acid residues in positions 1, 4, 7, 10, 18, 20 and 25 as shown in FIG. 1 are substituted with the corresponding amino acid residues of LTB as shown in FIG. 1.

4. A structural gene coding for a hybrid protein molecule according to claim 1.

5. A plasmid containing a structural gene according to claim 4.

6. An immunogenic protein comprising a hybrid protein molecule according to claim 1.

7. The immunogenic protein according to claim 6, wherein said protein is a fusion protein of said hybrid protein molecule and an amino-acid sequence of or from a prokaryotic or eukaryotic cell or a virus.

8. A vaccine comprising as an immunising component an immunologically effective amount of an immunogenic protein according to claim 6.

9. A vaccine comprising as an immunising component an immunologically effective amount of an immunogenic protein according to claim 7.

10. The vaccine according to claim 8, wherein said vaccine is against enterotoxin-induced illness.

11. The vaccine according to claim 9, wherein said vaccine is against enterotoxin-induced illness.

12. A method of reducing the incidence of enterotoxin-induced illness in an individual comprising administration to said individual of an immunologically effective amount of an immunogenic protein according to claim 6.

13. A method of reducing the incidence of enterotoxin-induced illness in an individual comprising administration to said individual of an immunologically effective amount of an immunogenic protein according to claim 7.

* * * * *

UNITED STATES PATENT AND TRADEMARK OFFICE
CERTIFICATE OF CORRECTION

PATENT NO. : 6,019,973
DATED : February 1, 2000
INVENTOR(S) : Jan HOLMGREN, et al.

It is certified that error appears in the above-identified patent and that said Letters Patent is hereby corrected as shown below:

ON THE TITLE PAGE:

Item

[76] Inventors, change " GOBORG" to --GOTEBORG--.

Signed and Sealed this

Second Day of January, 2001

Attest:

Q. TODD DICKINSON

Attesting Officer

Commissioner of Patents and Trademarks

UNITED STATES PATENT AND TRADEMARK OFFICE
CERTIFICATE OF CORRECTION

PATENT NO.    : 6,019,973
DATED         : February 1, 2000
INVENTOR(S)   : Jan Holmgren et al.

It is certified that error appears in the above-identified patent and that said Letters Patent is hereby corrected as shown below:

Title page,
Item [76], Inventors, change "Goborg" to -- Goteborg --.

Column 15,
Line 45, please delete claim 1 and replace with
-- 1.  A hybrid protein molecule consisting of heat-labile enterotoxin B subunit (LTB) and cholera toxin B subunit (CTB), which comprises an amino acid sequence which i composed of (a)   the amino acid sequence of mature CTB as shown in FIG. 1 in which amino acid residues are substituted with corresponding amino acid residues of mature LTB as shown in FIG. 1 which impart LTB-specific epitope characteristics to said immunogenic mature CTB; or (b)   the amino acid sequence of mature LTB as shown in FIG. 1 which amino acid residues are substituted with corresponding amino acid residues of mature CTB as shown in FIG. 1 which impart CTB-specific epitope characteristics to said immunogenic mature LTB. --

Signed and Sealed this

Eighteenth Day of May, 2004

JON W. DUDAS
*Acting Director of the United States Patent and Trademark Office*

SEQUENCE LISTING

<160> NUMBER OF SEQ ID NOS: 6

<210> SEQ ID NO 1
<211> LENGTH: 123
<212> TYPE: PRT
<213> ORGANISM: Vibrio cholerae

<400> SEQUENCE: 1

```
Met Ile Lys Leu Lys Phe Gly Val Phe Phe Thr Val Leu Leu Ser Ser
1               5                   10                  15

Ala Tyr Ala His Gly Thr Gln Asn Ile Thr Asp Leu Cys Ala Glu Tyr
            20                  25                  30

His Asn Thr Gln Ile His Thr Leu Asn Asp Lys Ile Phe Ser Tyr Thr
        35                  40                  45

Glu Ser Leu Ala Gly Lys Arg Glu Met Ala Ile Ile Thr Phe Lys Asn
    50                  55                  60

Gly Ala Thr Phe Gln Val Glu Val Pro Gly Ser Gln His Ile Asp Ser
65                  70                  75                  80

Gln Lys Lys Ala Ile Glu Arg Met Lys Asp Thr Leu Arg Ile Ala Tyr
                85                  90                  95

Leu Thr Glu Ala Lys Val Glu Lys Leu Cys Val Trp Asn Asn Lys Thr
            100                 105                 110

Pro His Ala Ile Ala Ala Ile Ser Met Ala Asn
        115                 120
```

<210> SEQ ID NO 2
<211> LENGTH: 123
<212> TYPE: PRT
<213> ORGANISM: Eschcerichia coli

```
<400> SEQUENCE: 2

Met Asn Lys Val Lys Phe Tyr Val Leu Phe Thr Ala Leu Leu Ser Ser
 1               5                  10                  15

Leu Cys Ala His Gly Ala Gln Ser Ile Thr Glu Leu Cys Ser Glu Tyr
             20                  25                  30

His Asn Thr Gln Ile Tyr Thr Ile Asn Asp Lys Ile Leu Ser Tyr Thr
         35                  40                  45

Glu Ser Met Ala Gly Lys Arg Glu Met Val Ile Thr Phe Lys Ser
 50                  55                  60

Gly Ala Thr Phe Gln Val Glu Val Pro Gly Ser Gln His Ile Asp Ser
 65                  70                  75                  80

Gln Lys Lys Ala Ile Glu Arg Met Lys Asp Thr Leu Arg Ile Thr Tyr
                 85                  90                  95

Leu Thr Glu Thr Lys Ile Asp Lys Leu Cys Val Trp Asn Asn Lys Thr
            100                 105                 110

Pro Asn Ser Ile Ala Ala Ile Ser Met Glu Asn
            115                 120

<210> SEQ ID NO 3
<211> LENGTH: 375
<212> TYPE: DNA
<213> ORGANISM: Eschcerichia coli

<400> SEQUENCE: 3
atgaataaag taaaatttta tgttttattt acggcgttac tatcctctct atgtgcacac      60
ggagctcctc agtctattac agaactatgt tcggaatatc acaacacaca aatatatacg    120
ataaatgaca agatactatc atatacggaa tcgatggcag gcaaagaga aatggttatc     180 attacattta gagcggcgc aacatttcag gtcgaagtcc cgggcagtca acatatagac     240
tcccaaaaaa aagccattga aggatgaag gacacattaa gaatcacata tctgaccgag    300
accaaaattg ataaattatg tgtatggaat aataaaaccc ccaattcaat tgcggcaatc    360
agtatggaaa actag                                                     375

<210> SEQ ID NO 4
<211> LENGTH: 375
<212> TYPE: DNA
<213> ORGANISM: Vibrio cholerae

<400> SEQUENCE: 4
atgattaaat taaaatttgg tgttttttttt acagttttac tatcttcagc atatgcacat    60
ggaacacctc aaaatattac tgatttgtgt gcagaatacc acaacacaca aatacatacg    120
ctaaatgata agatattttc gtatacagaa tctctagctg gaaaaagaga gatggctatc    180
attactttta gaatggtgc aacttttcaa gtagaagtac caggtagtca acatatagat     240
tcacaaaaaa aagcgattga aggatgaag gatacctga ggattgcata tcttactgaa     300
gctaaagtcg aaaagttatg tgtatggaat aataaaacgc ctcatgcgat tgccgcaatt   360
agtatggcaa attaa                                                    375

<210> SEQ ID NO 5
<211> LENGTH: 102
<212> TYPE: PRT
<213> ORGANISM: Vibrio cholerae

<400> SEQUENCE: 5

Thr Gln Asn Ile Thr Asp Leu Cys Ala Glu Tyr His Asn Thr Gln Ile
```

-continued

```
                1               5                      10                     15

His Thr Leu Asn Asp Lys Ile Phe Ser Tyr Thr Glu Ser Leu Ala Gly
            20                      25                     30

Lys Arg Glu Met Ala Ile Ile Thr Phe Lys Asn Gly Ala Thr Phe Gln
            35                      40                     45

Val Glu Val Pro Gly Ser Gln His Ile Asp Ser Gln Lys Lys Ala Ile
            50                      55                     60

Glu Arg Met Lys Asp Thr Leu Arg Ile Ala Tyr Leu Thr Glu Ala Lys
65                      70                      75                     80

Val Glu Lys Leu Cys Val Trp Asn Asn Lys Thr Pro His Ala Ile Ala
                    85                      90                     95

Ala Ile Ser Met Ala Asn
                    100

<210> SEQ ID NO 6
<211> LENGTH: 102
<212> TYPE: PRT
<213> ORGANISM: Escherichia coli

<400> SEQUENCE: 6

Ala Gln Ser Ile Thr Glu Leu Cys Ser Glu Tyr His Asn Thr Gln Ile
1               5                      10                     15

Tyr Thr Ile Asn Asp Lys Ile Leu Ser Tyr Thr Glu Ser Met Ala Gly
            20                      25                     30

Lys Arg Glu Met Val Ile Ile Thr Phe Lys Ser Gly Ala Thr Phe Gln
            35                      40                     45

Val Glu Val Pro Gly Ser Gln His Ile Asp Ser Gln Lys Lys Ala Ile
            50                      55                     60

Glu Arg Met Lys Asp Thr Leu Arg Ile Thr Tyr Leu Thr Glu Thr Lys
65                      70                      75                     80

Ile Asp Lys Leu Cys Val Trp Asn Asn Lys Thr Pro Asn Ser Ile Ala
                    85                      90                     95

Ala Ile Ser Met Glu Asn
                    100
```